(12) United States Patent
Slater

(10) Patent No.: US 9,277,932 B2
(45) Date of Patent: Mar. 8, 2016

(54) ENDOSCOPIC SCISSORS INSTRUMENT WITH FRICTION ENHANCING TISSUE STOPS

(75) Inventor: Charles R. Slater, Fort Lauderdale, FL (US)

(73) Assignee: Slatr Surgical Holdings LLC, Fort Lauderdale, FL (US)

( * ) Notice: Subject to any disclaimer, the term of this patent is extended or adjusted under 35 U.S.C. 154(b) by 752 days.

(21) Appl. No.: 12/471,024

(22) Filed: May 22, 2009

(65) Prior Publication Data

US 2010/0298852 A1    Nov. 25, 2010

(51) Int. Cl.
*A61B 17/32* (2006.01)
*A61B 17/3201* (2006.01)
*A61B 17/00* (2006.01)
*A61B 17/28* (2006.01)

(52) U.S. Cl.
CPC ..... *A61B 17/320016* (2013.01); *A61B 17/3201* (2013.01); *A61B 2017/00858* (2013.01); *A61B 2017/2825* (2013.01)

(58) Field of Classification Search
CPC ............. A61B 17/3201; A61B 17/295; A61B 17/282; A61B 17/320016; A61B 2017/2825; A61B 2017/2936; A61B 2017/320064
USPC .................. 606/174, 170, 205, 207
See application file for complete search history.

(56) References Cited

U.S. PATENT DOCUMENTS

| | | | |
|---|---|---|---|
| 2,012,648 A * | 8/1935 | Wheeler | 30/134 |
| 2,052,870 A * | 9/1936 | Coco | 606/120 |
| 2,172,490 A | 9/1939 | Archibald | |
| 2,490,414 A * | 12/1949 | Carney | 30/230 |
| 2,814,869 A * | 12/1957 | Matson | 30/124 |
| 3,323,208 A * | 6/1967 | Hurley, Jr. | 606/120 |
| 5,203,785 A | 4/1993 | Slater | |
| 5,439,471 A * | 8/1995 | Kerr | 606/174 |
| 5,439,478 A | 8/1995 | Palmer | |
| 5,496,347 A | 3/1996 | Hashiguchi et al. | |
| 5,499,992 A | 3/1996 | Meade et al. | |
| 5,499,997 A | 3/1996 | Sharpe et al. | |
| 5,700,270 A | 12/1997 | Peyser et al. | |
| 5,700,276 A | 12/1997 | Benecke | |
| 5,758,422 A * | 6/1998 | Frank | 30/230 |
| 5,893,874 A | 4/1999 | Bourque et al. | |
| 5,904,702 A | 5/1999 | Ek et al. | |
| 5,984,938 A | 11/1999 | Yoon | |
| 6,015,412 A | 1/2000 | Mifsud | |
| 6,027,522 A | 2/2000 | Palmer | |
| 6,059,799 A | 5/2000 | Aranyi et al. | |
| 6,159,162 A | 12/2000 | Kostylev et al. | |
| 6,206,877 B1 | 3/2001 | Kese et al. | |
| 6,409,727 B1 | 6/2002 | Bales et al. | |
| 6,554,844 B2 | 4/2003 | Lee et al. | |
| 6,634,105 B2 * | 10/2003 | Lindermeir | 30/135 |
| 6,773,434 B2 | 8/2004 | Ciarrocca | |
| 7,572,256 B2 | 8/2009 | Quick | |
| 2003/0036679 A1 * | 2/2003 | Kortenbach et al. | 600/104 |
| 2005/0101991 A1 | 5/2005 | Ahlberg et al. | |
| 2005/0192598 A1 * | 9/2005 | Johnson et al. | 606/148 |
| 2007/0244515 A1 | 10/2007 | Fanous | |

* cited by examiner

*Primary Examiner* — Kathleen Holwerda
*Assistant Examiner* — Sarah Simpson
(74) *Attorney, Agent, or Firm* — Gordon & Jacobson, P.C.

(57) ABSTRACT

An endoscopic instrument includes an end effector assembly having first and second scissors blades mounted on the clevis. Laterally offset from the cutting edges a tissue stop is provided on each tissue receiving surface to hold and/or put traction on tissue. The tissue stop may include tenaculum or saw-like projections.

17 Claims, 5 Drawing Sheets

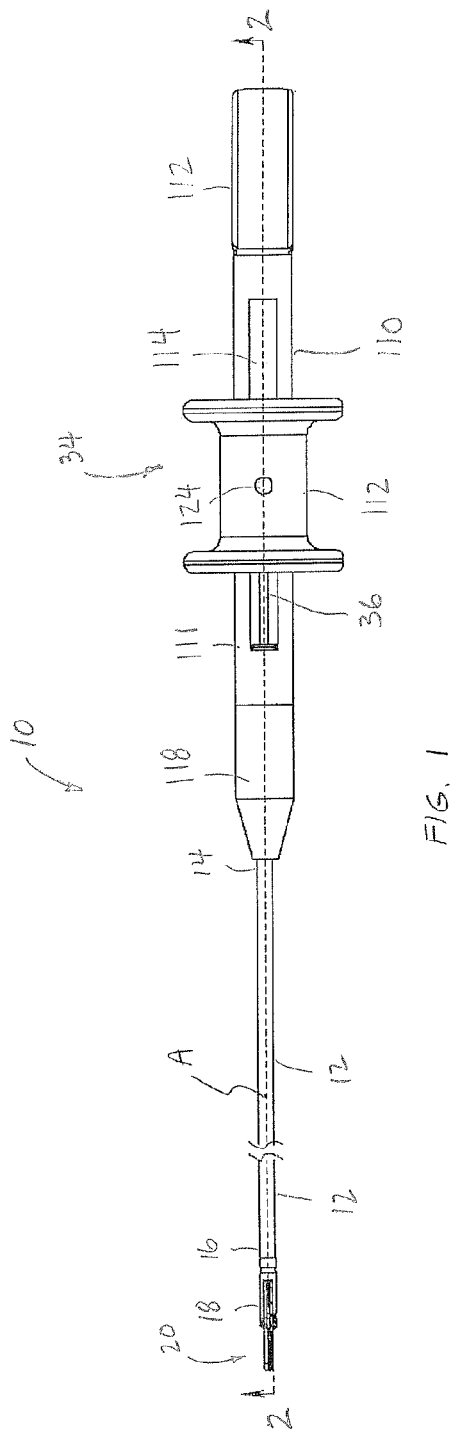
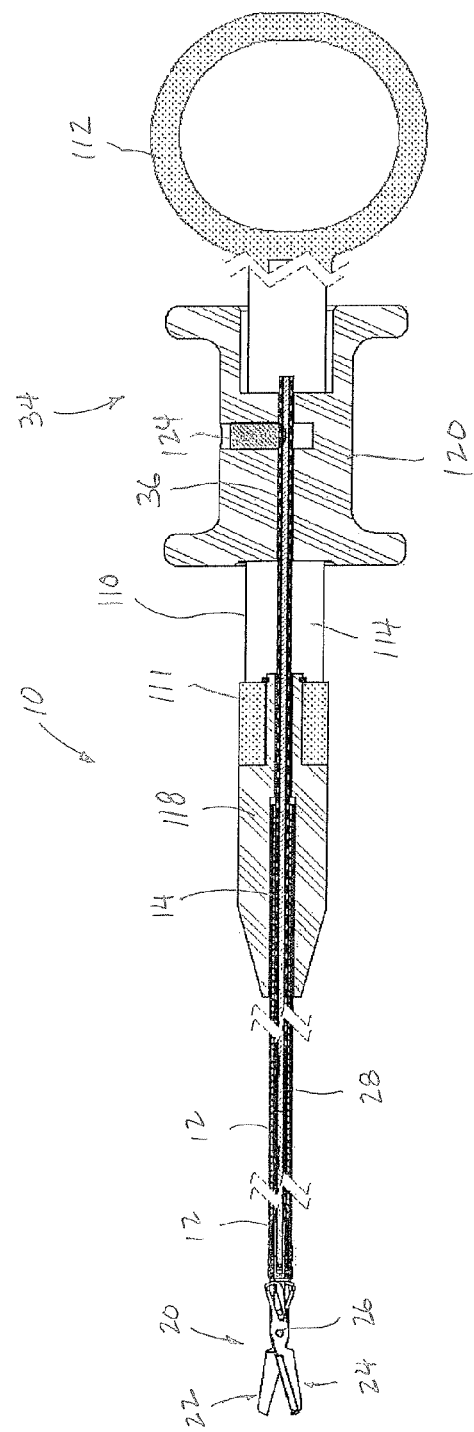
FIG. 1
FIG. 2

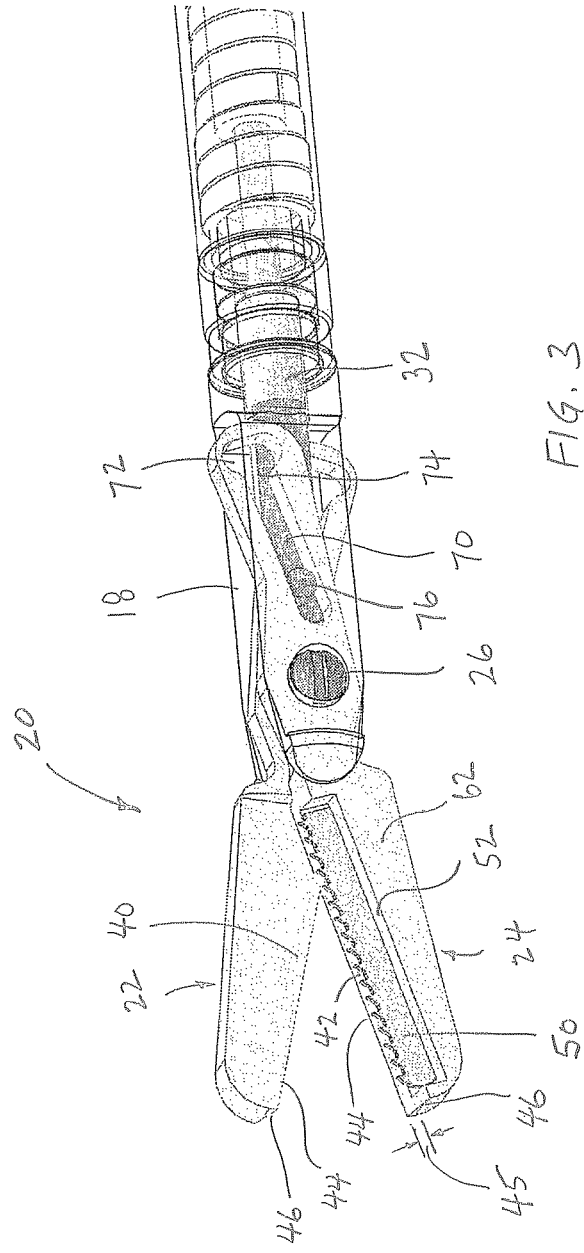
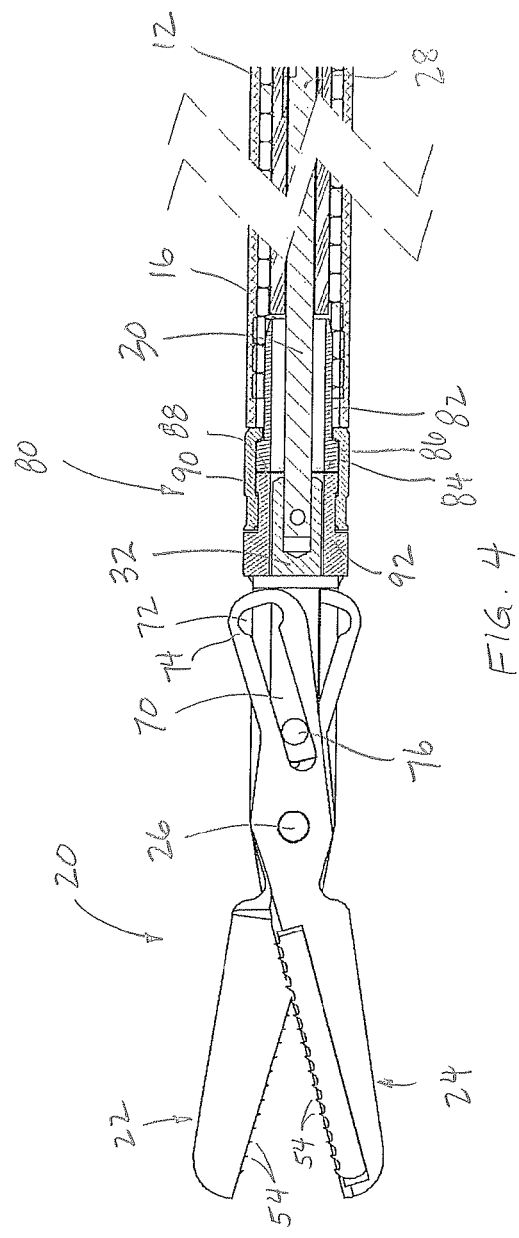

ENDOSCOPIC SCISSORS INSTRUMENT WITH FRICTION ENHANCING TISSUE STOPS

BACKGROUND OF THE INVENTION

1. Field of the Invention

This invention relates broadly to surgical instruments. More particularly, this invention relates to a flexible endoscopic scissors device insertable through a lumen of an endoscope.

2. State of the Art

Endoscopy is a minimally invasive medical procedure that assesses the interior of the human body using an endoscope. An endoscope generally consists of a rigid or flexible tube, an fiber optic illumination system to guide light provided by a light source through the tube of the endoscope in order to illuminate the organ or object under inspection, and a viewing system for collecting an image of the organ or object under inspection and for recording the image on an internal CCD device (video-endoscope) or for transmitting the image through the tube via a fiber optic bundle to an external video processor for viewing (fiber-endoscope). The endoscope can include one or more "working" channels (typically 2-4 mm in diameter) having a surgeon-accessible entry port through which specialized medical instruments can be passed into the working channels of the endoscope and into the field of view. Such specialized instruments (which can include graspers, biopsy forceps, scissors, etc.) can be used to grasp tissue, sample tissue for biopsy, or separate tissue, all from the inside of the body.

Laparoscopy is a minimally invasive surgical technique in which operations in the abdomen or thorax are performed through small incisions (usually 0.5-1.5 cm) via a rigid or flexible laparoscope. There are generally two types of laparoscopes, including a telescopic rod lens system that is usually connected to a video camera (single chip or three chip) and a digital laparoscope where the camera is placed at the end of the laparoscope, thus eliminating the rod lens system. A fiber optic cable system connected to a light source (halogen or xenon is inserted through a surgical port to illuminate the operative field for viewing. The abdomen is usually insufflated with carbon dioxide gas to create a working and viewing space. Specialized surgical instruments can be introduced into the abdomen or thorax through a surgical port in order to take biopsies and retrieve organs (or pieces thereof) and/or foreign objects from the inside of the body.

The surgical instruments used for endoscopy and laparoscopy generally include end effector means mounted adjacent the distal end of a tube or coil. Handles (or other actuation control means) are mounted to the proximal end of the tube or coil and move an actuator axially through the tube or coil. The distal end of the actuator is mechanically coupled to the end effector means in a manner that transforms the axial movement of the actuator into the desired movement of the end effector means. Such specialized endoscopic and laparoscopic surgical instruments are collectively referred to herein as endoscopic surgical instruments or endoscopic instruments, and endocope(s) and laparoscope(s) and collectively referred to herein as endoscopes. These general principles apply to most endoscopic instruments, but specific endoscopic instruments differ in length, size, stiffness, as well as other characteristics as the instruments are typically designed for a particular application as such instruments can be used for a wide variety of minimally invasive surgical procedures, including the endoscopic and laparoscopic applications summarized above.

SUMMARY OF THE INVENTION

The invention provides an endoscopic instrument having scissors blades and structure adapted to hold tissue from sliding forward along the blades, such structure offset from the cutting edges of the blades.

The invention also provides end effectors with a cam-slot and cam-pin operation and allows the end effectors to rotate together in the same direction when fully closed so as to traverse a non-flexible bend at the entry port of a working channel of an endoscope.

The invention additionally provides a high degree of accurate rotational manipulation of the end effector about the longitudinal axis of the device in a manner so that the end effector can be rotated even within a retroflexed endoscope.

According to the invention, an endoscopic instrument includes an elongate flexible tubular member having a proximal end and a distal end, a clevis at the distal end of the tubular member, and an end effector having first and second elements, such as scissors blades or grasping jaws, pivotally mounted on an axle on the clevis. A control member is axially movable through the tubular member, and a distal end of the control member is provided with a push rod that is coupled to the end effector elements to effect relative movement of the elements in an opposing opening and closing action as the control member is longitudinally translated back and forth within the tubular member. A proximal handle assembly is coupled to the proximal ends of the tubular member and the control member to permit longitudinal movement of the control member within the tubular member, and optionally rotation of the control member relative to the tubular member, as discussed further below.

According to one aspect of the invention, laterally offset from the cutting edges at least one of the blades of an endoscopic scissors, and preferably both of the blades, includes a friction enhancing tissue stop that functions to hold and/or put traction on tissue previous to, or while, cutting the tissue. In one embodiment, the tissue stop includes at least one set of tenaculum or grasping needle points provided at the distal end of the blade and/or as well as a position intermediate the proximal and distal ends. In another embodiment, the tissue stop includes a row of saw-like projections mounted adjacent (or "with close proximity") to the cutting edge of the blades. Each tissue stop is a distinct structure from the blade provided as a separate component on or within the ground or lateral surface of the scissor blade, and are mechanically bonded thereat.

In a second aspect of the invention the proximal end of preferably each end effector element and the distal end of the control member are coupled together in a cam-pin and cam-slot assembly. As such, the distal end of the control member includes a cam-pin that extends into a cam-slot in the proximal end of each element. As the control member is translated, the cam-pin rides in the cam-slots causing the end effector elements to collectively move in an opposing opening and closing action. Relative proximal movement of the control member thus causes the end effector elements to move into a closed configuration. According to this aspect of the invention, the proximal end of the cam slot includes a bilaterally widened area (on both sides of the longitudinal axis of the cam slot so that when the pin is fully retracted into the bilaterally widened area the end effector elements are now free to rotate together in the same direction. This effectively shortens the rigid non-bendable length of the end effector allowing for insertion of a longer-than-usual end effector which previously would not have been passable into and through the entry portion of the endoscope.

According to another aspect of the invention, the end effector of the endoscopic instrument is rotatable about the axis of the tubular member by rotation of the control member, as actuated from the proximal handle. According to another aspect of the invention, to permit such rotation, the distal end of the tubular member is provided with a stationary inner bearing, and the clevis for the end effectors is rotatably secured to an outer bearing that rotates on the inner bearing. The torque applied to the control member is transferred to the push rod and cam pin at the distal end thereof. As a result of the applied torque, the end effectors and clevis smoothly rotate at the interface of the inner and outer bearings.

According to yet another aspect of the invention, the control member has decreasing torsional and flexural stiffness from the proximal towards the distal portions of its length. The control member is preferably constructed of a proximal portion and a distal portion and a coupling element that mechanically joins the proximal and distal portions. The proximal portion is a composite carbon rod or a spring steel stainless wire. The distal portion is a thin multi-strand, drawn brazed strand cable or a single superelastic metal wire. The distal portion is capable of offering significant resilient flexibility, as well as accurate and directionally even application of torque—both clockwise and counterclockwise—without causing jump or whip (uneven or sudden rotation). The coupling element is preferably a portion of hypotube provided at the adjacent ends of the proximal and distal portions, although it may include other devices or methods as well as threading, welding, etc.

Additional advantages of the invention will become apparent to those skilled in the art upon reference to the detailed description taken in conjunction with the provided figures.

BRIEF DESCRIPTION OF THE DRAWINGS

FIG. 1 is a side elevation view of an endoscopic instrument according to the invention.

FIG. 2 is a longitudinal section of the endoscopic instrument of FIG. 1 taken along line 2-2 in FIG. 1.

FIG. 3 is a partially transparent isometric view of the distal end of the endoscopic instrument of FIG. 1.

FIG. 4 is a broken partial section view of the distal end of the endoscopic instrument of FIG. 1.

DETAILED DESCRIPTION OF THE PREFERRED EMBODIMENTS

Figure 5:
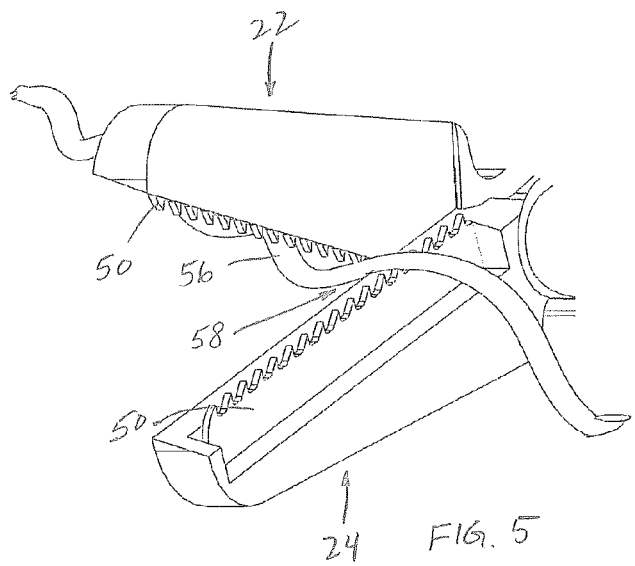
FIG. 5 is an isometric view of endoscopic scissors blades with a first embodiment of tissue stops coupled to the blades of the endoscopic instrument and showing the use of the tissue stops to retain a blood vessel.

Turning now to FIGS. 1 through 4, an endoscopic instrument 10 according to the invention is shown. The endoscopic instrument 10 includes an elongate tubular member 12 preferably of a flexible construction having a proximal end 14 and a distal end 16, a clevis 18 rotatably mounted at the distal end 16 of the tubular member 12, and an end effector assembly 20 dimensioned for passage within the working channel of an endoscope. A control member 28 is axially displaceable through and rotatable within the tubular member 12. The distal end 30 of the control member 28 is provided with a push rod 32 that is coupled to the end effector 20 to effect relative movement of the end effector in an opening and closing action, e.g., scissoring action, as the control member 28 is longitudinally translated within the tubular member 12, as discussed in more detail below. A proximal handle assembly 34 is coupled to the proximal end 14 of the tubular member 12 and the proximal end 36 of the control member 28 to effect relative longitudinal and rotational movement of the control member 28 and the tubular member 12, as discussed further below.

Referring to FIGS. 3 and 4, in the embodiment shown, the end effector assembly 20 is a scissors assembly including scissors blades 22, 24 pivotally mounted on an axle 26 at the clevis 18. The blades 22, 24 each include a medial surface 40, a ground (or honed) surface 42, which extends to, and ends in a sharp cutting edge 44 at an intersection with the medial surface, and a lateral surface 62 opposite the medial surface. The cutting edge 44 extends from a location distal the pivot point to the distal end 46 of the blade.

According to one aspect of the invention, preferably at least one blade, and more preferably both blades, includes a friction enhancing tissue stop 50 that is laterally offset by an offset 45 from the cutting edge 44 (so as not to be present at the cutting edge at all). The offset 45 is preferably less than 0.25 mm (0.012 inch) but may be a full blade-thickness offset from the cutting edge such that the tissue stop is mechanically attached to the lateral surface 62. The tissue stop 50 functions to hold and/or put traction on tissue without cutting the biological tissue, to hold or put traction on non-metallic articles such as sutures without cutting the same, and to not interfere with the cutting edge 44 of the blade. It is advantageous that at least a portion of the tissue stop can be provided proximal to the distal end 46 of the scissors blade to stably retain tissue and prevent its advancement down the ground surface 42 to the distal end 46 of the blade. Each tissue stop 50 may be provided as an insert within a respective recess 52 that extends within the lateral side 62 of the respective blades 22, 24. Each tissue stop 50 is retained in its recess 52 preferably by welding, bonding, brazing, riveting or another mechanical bonding or fit. Optionally, the tissue stops 50 may be manufactured from a different material than the material or materials defining the blades 22, 24. By way of example only, while the blades 22, 24 are preferably constructed of metal, the tissue stops 50 may be constructed of the same metal, a different metal, a carbon composite or a polymer composite. The tissue stops may be readily shaped by molding, casting, machining, photo-etching, forming or stamping. In an embodiment, the tissue stops 50 are each a rigid, sheet-form structure discrete from the scissors blades and attached thereto.

Figure 6:
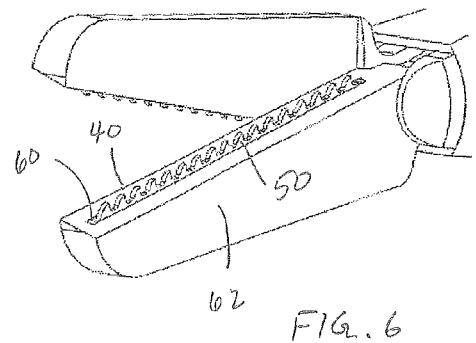
FIG. 6 is an isometric view of endoscopic scissors blades with a second embodiment of tissue stops coupled to the blades of the endoscopic instrument.

By way of example, in the embodiment shown in FIGS. 3 through 5, the tissue stops 50 are provided on both of the scissors blades 22, 24 and include a continuous row of saw-like toothed projections 54. The projections are not of sufficient height above the cutting edge 44 or sharpness to cut through tissue. The projections function to assist in holding slippery tissue, including blood vessels such as artery 56 in place even in the rear-most position of the open scissors blades 22, 24, e.g., at 58, and prevent the common occurrence of such tissue from sliding forward and out from between the blades as the blades are moved into a closed position. Turning to FIG. 6, the tissue stops 50 may alternatively be received within a slot 60 in the ground surface 42 (with both the medial side 40 and lateral side 62 of the blade enclosing portions of the stop). The stop functions in the same manner as described above. As yet another alternative, the tissue stops 50 may be mounted external the blade on the lateral side 62.

Figure 7:
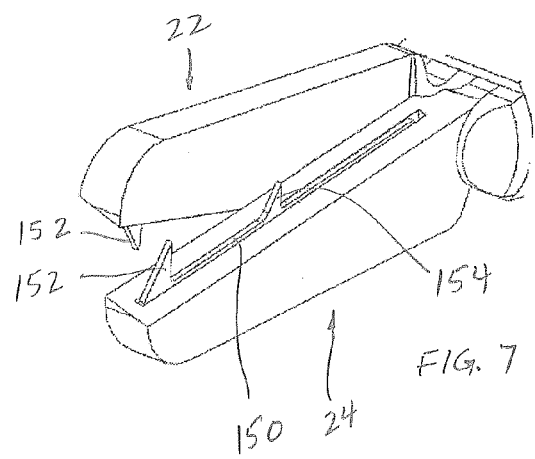
FIG. 7 is an isometric view of endoscopic scissors blades with a third embodiment of tissue stops coupled to the blades of the endoscopic instrument.
Figure 8:
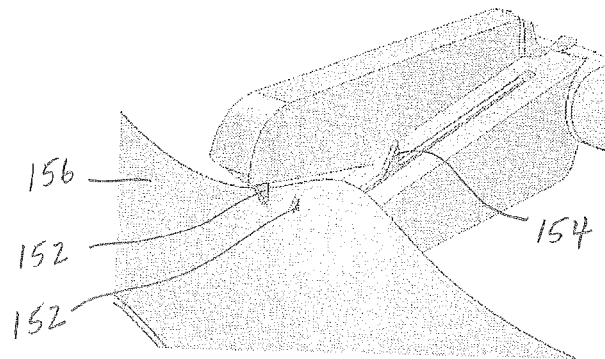
FIG. 8 illustrates the use of the tissue stops of FIG. 7 to engage tissue.

Referring now to FIG. 7, another embodiment of a tissue stop 150 is shown in combination with each scissors blade 22, 24. Each tissue stop 150 includes a first tenaculum (or grasping needle point) 152 provided adjacent, but proximally displaced relative to the distal end of its respective blade (e.g., blade 24), as well as a second tenaculum 154 at a position intermediate the proximal and distal ends of the blade. In each stop 150, the distal tenaculum 152 preferably extends a greater height from the ground surface 42 and is larger than the more proximal tenaculum 154. As shown in FIG. 8, the distal tenaculum 152 is readily adapted to effectively pierce and maneuver tissue 154, whereas the more proximal tenaculum 154 is configured to prevent tissue from sliding down the ground surface 42 toward the distal end 46 of the blade 24.

Figure 9:
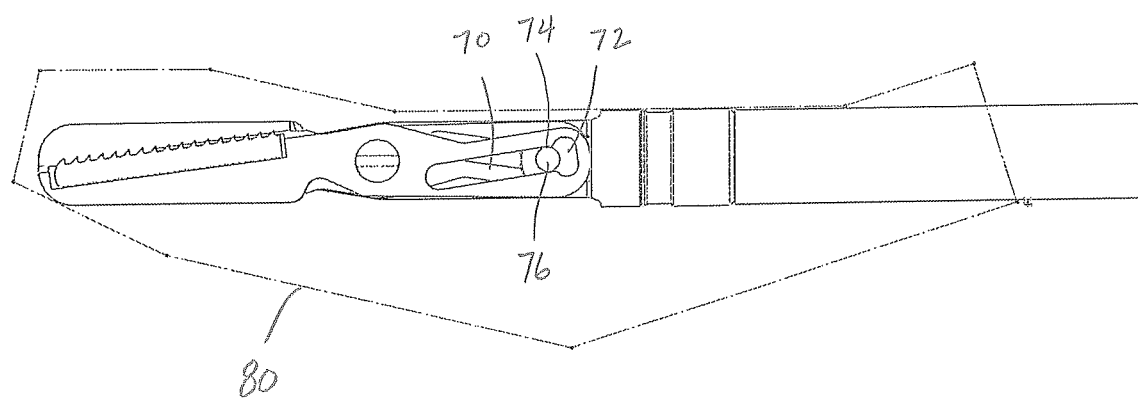
FIGS. 9 and 10 are schematic illustrations of the operation of the cam-pin and cam-slot arrangement of the endoscopic instrument.
Figure 10:
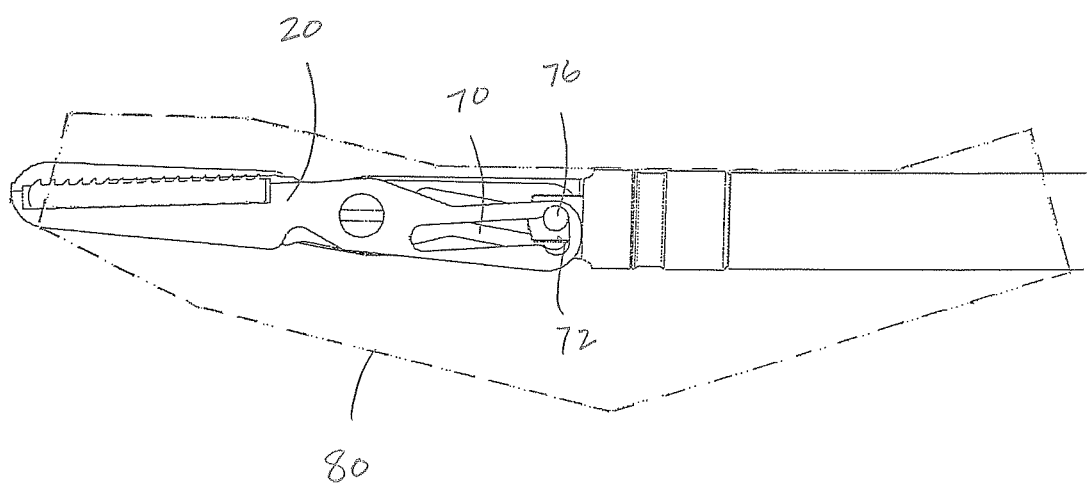

Referring back to FIGS. 3 and 4, the blade end effector elements 22, 24 of the end effector assembly 20 are moved between open and closed positions via a cam-pin and cam-slot assembly. More specifically, the proximal end of each blade 22, 24 (proximal of the axle 26) includes a longitudinally extending cam-slot 70 (shown best with respect to blade 24) that is oriented at an oblique angle relative to the longitudinal axis A of the tubular member 12. The cam-slot 70 includes a bilaterally widened area 72 (on both sides of the axis of the cam-slot), preferably located at the proximalmost end 74 of the cam-slot. The push rod 32 joined to the distal end 30 of the control member 28 includes and is provided with a transverse cam-pin 76 that rides in the cam-slot 70 of each of the blades 22, 24. As the control member 28 is translated within the tubular member 12 by operation of the proximal handle assembly 34, the cam-pin 76 is caused to ride within the cam-slots 70 causing the blades 22, 24 to move in a scissoring action, with relative proximal movement of the control member causing the blades to move into a closed configuration, as shown in FIG. 9. In the closed configuration shown in FIG. 9 the scissors blades are rigidly held by the tolerances of the cam-pin and cam-slot arrangement to define a stiff 'non-giving' assembly about the clevis 18 (FIG. 3). This can present difficulty in maneuvering the end effector assembly, particularly where longer scissors blades or other longer end effectors are used, through the relatively rigid and bent entry port 80 (shown in broken lines) of a working channel of an endoscope. However, as shown in FIG. 10, when the cam-pin is further retracted into the bilaterally widened area 72 at the proximal end 74 of the cam-slot 70, sufficient room is provided for the cam-pin to permit the blades 22, 24 of the end effector assembly 20 to rotate together in the same direction about the longitudinal axis A of the instrument. This effectively shortens the rigid non-bendable length of the end effector assembly 20 allowing for passage of a longer end effector assembly 20 into the entry portion 80 of a working channel of an endoscope. As such, as shown in FIG. 10, a longer rigid end effector 20 operated by a cam-pin and cam-slot arrangement can be used.

The end effector assembly 20 is rotatable about the axis of the tubular member 12 by rotation of the control member 28, as actuated from the proximal handle 30. Turning again back to FIG. 4, to facilitate effective and smooth rotation when the control member 28 is subject to a torque at the proximal handle assembly 30, the clevis is mounted to the tubular member with a rotational bearing assembly 80. More particularly, an inner bearing 82 is fixed to the distal end 16 of the tubular member either through bonding, welding or mechanical means such as crimping. The inner bearing 82 includes distal bearing surfaces extending from the distal end of the tubular member. The bearing surfaces include a distal face 84 and a circumferential face 86. The proximal face 88 of the clevis 18 rotatably bears against the distal face 84 of the inner bearing 82. An outer bearing 90 is rotatably mounted on said circumferential face 86 of said inner bearing 82 and is secured about a proximal portion 92 of the clevis 18, e.g., by crimping, to longitudinally secure the clevis in a smoothly rotatable manner to the inner bearing 82 and thus to the tubular member. Torque applied to the control member 28 is thus transferred to the push rod 32 and cam pin 76 at the distal end thereof to directly rotate the end effectors 22, 24 on 20 the clevis 18 about the distal end of the tubular member 16. Importantly, the torque is applied directly to the end effectors 22, 24, rather than the clevis 18 (from which the control member 28 is de-coupled).

Figure 11:
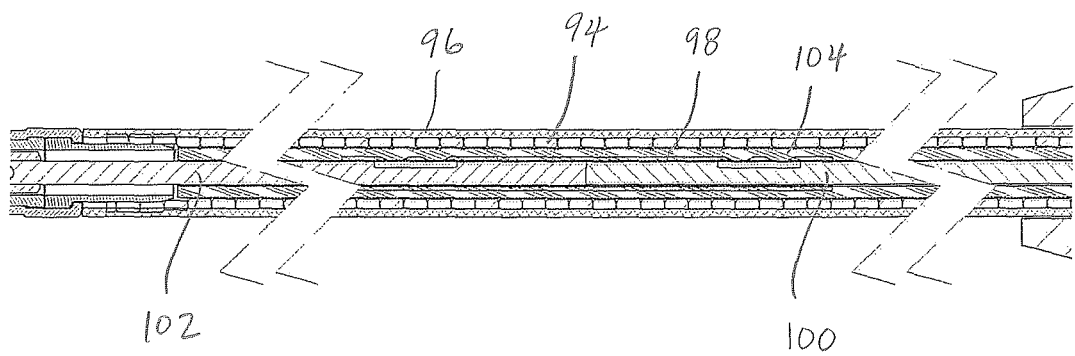
FIG. 11 is a broken section view of a central portion of the endoscopic instrument.

Referring now to FIG. 11, the tubular member 12 is preferably a flat or round wire wound coil 94 defining a flexible construct with a lubricious polymeric flexible outer jacket 96. The control member 28 is constructed to have different torsional and longitudinal stiffness along proximal and distal portions of its length. The control member 28 is preferably constructed of discrete proximal and distal portions that are joined with a coupling element 98, e.g., a short length of hypotube crimped to join such portions. The proximal portion 100 is preferably a single spring steel stainless wire or a flexible composite carbon rod, but could also be made from a bi-radially wound wire cable (wound in opposing directions like "speedometer" cable). The distal portion 102 has a length of 8 to 20 inches, and more preferably approximately 12 inches, and is a thin multi-strand cable of the above type or a drawn brazed strand (DBS) cable; i.e., a cable that has been drawn down in a die and brazed to bind the wires together to reduce the tendency of the cable to unwind if rotated against a load in the opposite direction of the winding. Alternatively, the distal portion is a single superelastic metal wire. The distal portion is capable of offering significant resilient flexibility, as well as accurate and directionally even application of torque—both clockwise and counterclockwise—without causing jump or whip (uneven or sudden rotation). The use of two discrete portions optimizes the control member in cost, function and repeatability. At the proximal portion of the instrument, the instrument remains relatively straight during use and the single steel wire or composite rod 100 is readily adapted to impart the longitudinal displacement and rotational torque from the proximal handle. The distal portion of the instrument can be subject to dramatic distortion as the instrument is bent through the tortuous path of a highly flexed (or even retroflexed) endoscope. A multistrand cable or superelastic wire is well-adapted to effect longitudinal displacement along such portion of the instrument as well as provide accurate and directionally even torque even while the distal end of the instrument is severely bent or retroflexed over. The distal end of the control member 28 is provided with the push rod 32, as discussed above, although other distal structure can be provided for attaching the control member to the end effectors. A polymeric tubular bearing 104 is provided between the control member 28 and the wound wire coil 94 to take up the space between the two elements and prevent buckling of the control member 28.

Referring back to FIGS. 1 and 2, the handle assembly 34 included a shaft 110 having a distal end 111, a proximal thumb ring 112 and a longitudinal slot 114. A ferrule 118 is rotatably mounted to a distal end 111 of the shaft 110 in communication with the longitudinal slot 114. The proximal end of the tubular member 14 is fixed within the ferrule 118. A finger spool 120 is longitudinally displaceable on the shaft 110 at the slot 114. The proximal end 122 of the control member is fixed with the spool 120, e.g., with a set screw 124. Longitudinal displacement of the spool 120 on the shaft causes longitudinal displacement of the control member 28 relative to the tubular member 12 and operation of the end effectors, as discussed above. Rotation of the shaft 110 and spool 120 relative to the ferrule 118 causes rotation of the control member 28 relative to the tubular member 12 and resultant rotation of the end effectors elements 22, 24 relative to the tubular member as also discussed above.

There have been described and illustrated herein embodiments of an endoscopic instrument. While particular embodiments of the invention have been described, it is not intended that the invention be limited thereto, as it is intended that the invention be as broad in scope as the art will allow and that the specification be read likewise. Thus, while the instrument has been described particularly with respect to a scissors device, it will be appreciated that numerous aspects of the device have application in other endoscopic instruments having end effectors other than scissor blades. For example, at least the cam-slot design, end effector rotatable bearing mount, and control member for operating the end effector are concepts applicable to endoscopic instruments in general, including graspers and forceps. In addition, while two exemplar off-set tissue stops have been disclosed with respect to scissor blades, other tissue stop designs in accord with the invention can be provided to the ground surface extension of the cutting edge as well the adjacent surface of the scissor blade opposite the medial surface. It will therefore be appreciated by those skilled in the art that yet other modifications could be made to the provided invention without deviating from its spirit and scope as claimed.

What is claimed is:

1. An endoscopic scissors instrument, comprising:
   a) a tubular member having proximal and distal ends and defining a longitudinal axis;
   b) a control member having proximal and distal ends and extending through said tubular member;
   c) a clevis coupled to the distal end of said tubular member;
   d) an end effector assembly comprising first scissors and second scissors blades, at least one of said scissors blades mounted to said clevis and movable relative to the other scissors blade, said distal end of said control member coupled to said at least one movable scissors blade, said first scissors blade having a medial surface, a ground surface, and a sharp cutting edge at an intersection of said medial and ground surfaces, and a lateral surface opposite said medial surface, and said second scissors blade having a medial surface, a ground surface, and a sharp cutting edge at an intersection of said medial and ground surfaces, and a lateral surface opposite said medial surface, and said at least one of said ground or lateral surfaces of said first and second scissors blades including a metal or a carbon composite, sheet-form friction enhancing tissue stop, discretely formed from the first and second scissors blades, that is configured to pierce into tissue located between said cutting edges of said first and second scissors blades as the tissue is cut by said cutting edges, said tissue stop mounted within or on said ground or lateral surfaces, extends laterally adjacent with at least a portion of said cutting edge of said respective blade, extends above said ground surface, and is laterally offset from said cutting edge of said respective blade; and
   e) a proximal handle assembly coupled to said proximal ends of said tubular member and said control member for moving said control member and said tubular member relative to each other to effect relative movement of the scissors blades between open and closed positions.

2. The endoscopic scissors instrument according to claim 1, wherein:
   said control member has decreasing torsional and flexural stiffness along its length from its proximal end towards its distal end.

3. The endoscopic scissors instrument according to claim 1, wherein:
   said at least one movable scissors blade includes a cam-slot, and said distal end of said control member is coupled to a cam-pin that rides in said cam-slot to effect movement of said scissors blades relative to each other between open and closed positions.

4. The endoscopic scissors instrument according to claim 3, wherein:
   both said first and second scissors blades are rotatably mounted to said clevis, and said cam slot in each of said scissors blades includes a proximal bilateral widening, such that when said cam pin is retracted to move said scissors blades into said closed position, further retraction of said cam pin into said bilateral widening permits said scissors blades to rotate together to one side of the longitudinal axis.

5. The endoscopic scissors instrument according to claim 1, wherein:
   said piercing tissue stop is configured to at least partially enter and hold tissue at the interior of a human body but does not engage in a shearing action with a like tissue stop to cause cutting of the tissue along a cutting edge.

6. The endoscopic scissors instrument according to claim 1, wherein:
   said ground surfaces of each of said first and second scissors blades receives a tissue stop.

7. The endoscopic scissors instrument according to claim 1, wherein:
   said tubular member is sufficiently elastically-flexible to be passed through a tortuous passage of a retroflexed endoscope.

8. The endoscopic scissors instrument according to claim 1, wherein:
   said at least one of said ground or lateral surfaces includes an opening extending in a proximal-distal direction, and said tissue stop is mounted in said opening.

9. The endoscopic scissors instrument according to claim 8, wherein:
   said opening is a slot.

10. The endoscopic scissors instrument according to claim 8, wherein:
    said opening is a recess open on said lateral side.

11. The endoscopic scissors instrument according to claim 1, wherein:
    said tissue stop is mechanically bonded to one of said first and second scissors blades.

12. The endoscopic scissors instrument according to claim 1, wherein:
    said ground surface includes an opening extending in a proximal-distal direction, and said tissue stop is mounted in said opening.

13. The endoscopic scissors instrument according to claim 12, wherein:
   said opening is a slot.

14. The endoscopic scissors instrument according to claim 1, wherein:
   said tissue stop includes a row of tooth-like projections that protrude above said cutting edge.

15. The endoscopic scissors instrument according to claim 14, wherein:
   said tooth-like projections are continuous serrations.

16. The endoscopic scissors instrument according to claim 1, wherein:
   said tissue stop includes pointed tenaculum that protrude above said cutting edge and are structured to pierce through tissue.

17. The endoscopic scissors instrument according to claim 1, wherein:
   said clevis is rotatably coupled to said tubular member, and
   said proximal handle is adapted to move said control member and said tubular member rotatably relative to each other to effect rotation of said scissors blades on said clevis about said longitudinal axis.

* * * * *